(12) United States Patent
Matthews

(10) Patent No.: US 6,168,274 B1
(45) Date of Patent: Jan. 2, 2001

(54) OPHTHALMOSCOPE AND ATTACHMENT THEREFOR

(75) Inventor: James Robert Arnold Matthews, Bracknell (GB)

(73) Assignee: Keeler Limited, Windsor (GB)

( * ) Notice: Under 35 U.S.C. 154(b), the term of this patent shall be extended for 0 days.

(21) Appl. No.: 09/393,429

(22) Filed: Sep. 10, 1999

Related U.S. Application Data
(60) Provisional application No. 60/108,624, filed on Nov. 16, 1998.

(51) Int. Cl.[7] ....................................................... A61B 3/10
(52) U.S. Cl. ............................................................ 351/221
(58) Field of Search ................................... 351/205, 206, 351/208, 210, 216, 221; 359/372, 375, 381, 382, 835

(56) References Cited

U.S. PATENT DOCUMENTS
4,723,842 * 2/1988 Twisselmann et al. ............... 350/511
5,713,047 * 1/1998 Kohayakawa ......................... 351/206

FOREIGN PATENT DOCUMENTS
33 12 606    10/1984 (DE) .
0 048 181    3/1982  (EP) .
2 167 919    6/1986  (GB) .

* cited by examiner

Primary Examiner—George Manuel
(74) Attorney, Agent, or Firm—Lee, Mann, Smith, McWilliams, Sweeney and Ohlson

(57) ABSTRACT

An ophthalmoscope has viewing optics through which, in use, the user views an eye under examination. Those optics include one or more light receiving elements (62 and 64). The ophthalmoscope also has a centrally positioned camera (14) for detecting an image corresponding to that seen by the user. Light is reflected into the camera objective by means of a reflector (16) which is also centrally positioned on the ophthalmoscope and is situated in substantially the same plane as said elements of the viewing optics, but is laterally spaced therefrom. The central positioning of the camera does not adversely affect the lateral weight distribution of the ophthalmoscope, whilst the provision of a reflector at the same level as the optical elements helps to preserve the congruents between the image detected by the camera and that seen by the user if the condenser lens (used to form the virtual image of the eye under examination) is moved towards or away from the ophthalmoscope.

12 Claims, 3 Drawing Sheets

OPHTHALMOSCOPE AND ATTACHMENT THEREFOR

RELATED APPLICATION

This Application claims the benefit of U.S. provisional Patent Application No. 60/108,624 filed on Nov. 16, 1998.

FIELD OF THE INVENTION

This invention relates to ophthalmoscopes, in particular to an indirect ophthalmoscope which is used by an ophthalmologist in the observation of an image of the retina of an eye under examination. The invention also relates to an attachment for an ophthalmoscope.

BACKGROUND TO THE INVENTION

It is known to fit an indirect ophthalmoscope with a camera for detecting an image of the retina being observed, through a condenser lens, by the user of the ophthalmoscope. Such ophthalmoscopes are often used in the instruction of students or to inform patients and their relatives, since the image of the retina being observed by an ophthalmologist using the device can be displayed on a separate video display unit in real time. The image can also be recorded for subsequent analysis. It is also envisaged that, with the advent of improved telecommunications systems, a non-specialist could use the ophthalmoscope to provide an image which is transmitted to a specialist at a remote location so that the specialist can perform an examination without visiting the patient.

Typically, an indirect ophthalmoscope is a binocular device having viewing optics which have two central mirrors arranged to direct respective images to the left and right eye of the person using the ophthalmoscope. In one known arrangement, the camera detects an image reflected from an angled half-silvered mirror disposed immediately in front of the two mirrors.

A disadvantage of this arrangement is that the half-silvered mirror reduces the intensity of light which reaches the viewing optics. in addition, the intensity of light reaching the camera is less than would be the case pith a fully silvered mirror. Given that there is, in practice, an upper limit to the intensity of light which can be used to illuminate the eye under examination, the image is seen by the person using the ophthalmoscope and detected by the camera may be less bright than is desired.

In addition, since the image detected by the camera has been reflected from the mirror, it is inverted relative to the image seen by the wearer, who would therefore have to take this into account when explaining features of the eye under examination to students viewing a display of the image detected by the camera.

Another known type of camera attachment for an ophthalmoscope is produced by Litechnica, and comprises a fully silvered mirror which reflects light into a camera attached to the side of the ophthalmoscope. However, this gives rise to a lop-sided arrangement and the mirror partially obscures the user's view of the eye under examination. It is also known to provide an ophthalmoscope with a centrally mounted camera (The Video Omega 2C produced by Heine Optotechnik) but in this case the images detected by the camera and seen by the user may become incongruent as a result of changes in the working distance of the ophthalmoscope.

SUMMARY OF THE INVENTION

According to a first aspect of the invention, there is provided an ophthalmoscope having viewing optics through which, in use, an eye under examination is viewed, the optics having at least one light receiving element via which light from an eye under examination is received by the viewing optics, the ophthalmoscope further comprising image detection apparatus for detecting an image of an eye under examination, wherein the image detection apparatus is substantially centrally positioned on the ophthalmoscope and is so positioned relative to the light receiving element that, in use, light from the eye under examination which is incident on the image detection means is received by the latter at a position which is laterally spaced from the paths of light from the eye to the light receiving element or through the viewing optics, wherein, said position is in the same horizontal plane as the light receiving element.

Thus, the image detection apparatus does not block the passage of any light from the eye to the light receiving element, and therefore does not reduce the intensity of the image viewed through the viewing optics. Similarly, the viewing optics do not affect the intensity of the image detected by the image detection apparatus. In addition, since the element and the position at which light is incident on the image detecting apparatus are at substantially the same level, the images seen by the user and detected by the apparatus are not displaced relative to each other by variations in the working distance of the ophthalmoscope.

Preferably, the image detection apparatus has a portion via which, in use, light from the eye under examination enters the image detection means, and which may be laterally spaced from the light receiving element.

Where the ophthalmoscope is a binocular instrument, having two spaced apart light receiving elements, the portion is preferably so situated that the elements are at least partially spaced in opposite lateral directions from the portion.

If the stereopsis of the ophthalmoscope is fixed, substantially all of each element is preferably laterally spaced from the portion. If, however, the separation of the elements is adjustable to adjust the stereopsis of the ophthalmoscope, substantially all of each element is preferably laterally spaced from the portion at least when the separation of the objectives is at its maximum.

Preferably, the portion is equidistant from the elements.

This helps to ensure that the image detected by the image detection system corresponds to that viewed through the viewing optics.

Preferably, the image detection apparatus comprises a camera, which is substantially centrally positioned on the ophthalmoscope, preferably in a position equidistant from the light receiving elements.

The substantially central mounting of the camera helps to reduce the effect that the camera has on the balance of the ophthalmoscope; the instrument is not lopsided, and is consequently easier to wear than the type of ophthalmoscope in which the camera is situated to one side of the viewing optics.

Said portion of the image detection means may comprise the objective of the camera.

Preferably, however, the portion comprises reflecting means which, in use, reflects the image of an eye under examination into the camera. Preferably the camera is positioned above the light receiving elements, and the reflecting means is at substantially the same level as said elements and reflects light up into the camera.

The reflecting means is conveniently so arranged as to cause two reflections of light from the eye under examination so as to eliminate any mirror inversion of the image detected by the camera.

The use of two reflections to avoid mirror inversions provides an effective and relatively cheap method of ensuring that the orientation of the image detected by the camera corresponds to that of the image seen through the viewing optics.

Conveniently, the reflecting means comprises a prism, preferably a pentagonal prism, for example a penta prism.

The pentagonal prism provides the double reflection and is particularly advantageous since the relative orientation of the prism surfaces which cause the two reflections is fixed and the prism provides is an efficient reflector of light.

Preferably, the prism and camera are carried by a frame adapted to be mounted on the front of the ophthalmoscope.

The invention also lies in an attachment for an ophthalmoscope, the viewing optics of which have at least one light receiving element via which light from an eye under examination enters the viewing optics, the attachment comprising retaining means for holding a camera and reflecting means operable to reflect light from an eye under examination into a camera held by the retaining means, the attachment further comprising mounting means for mounting the attachment on an ophthalmoscope, wherein the position of the reflecting means relative to the mounting means is such that, when mounted on an ophthalmoscope, the reflecting means is, in use, laterally spaced from, and at the same level as the light receiving element and the camera is substantially centrally positioned on the ophthalmoscope.

Preferably, the attachment is adapted for use with a binocular ophthalmoscope, and the retaining means comprises a frame having a cross-member on which the reflecting means is mounted in a generally central position such that, with the attachment mounted on the ophthalmoscope, the two light receiving elements of the latter are laterally spaced, in opposite directions, from the reflecting means.

Preferably, the reflecting means comprises a pentagonal prism, for example a penta prism.

BRIEF DESCRIPTION OF THE DRAWINGS

The invention will now be described, by way of example only, with reference to the accompanying drawings, in which.

DETAILED DESCRIPTION

Figure 1:
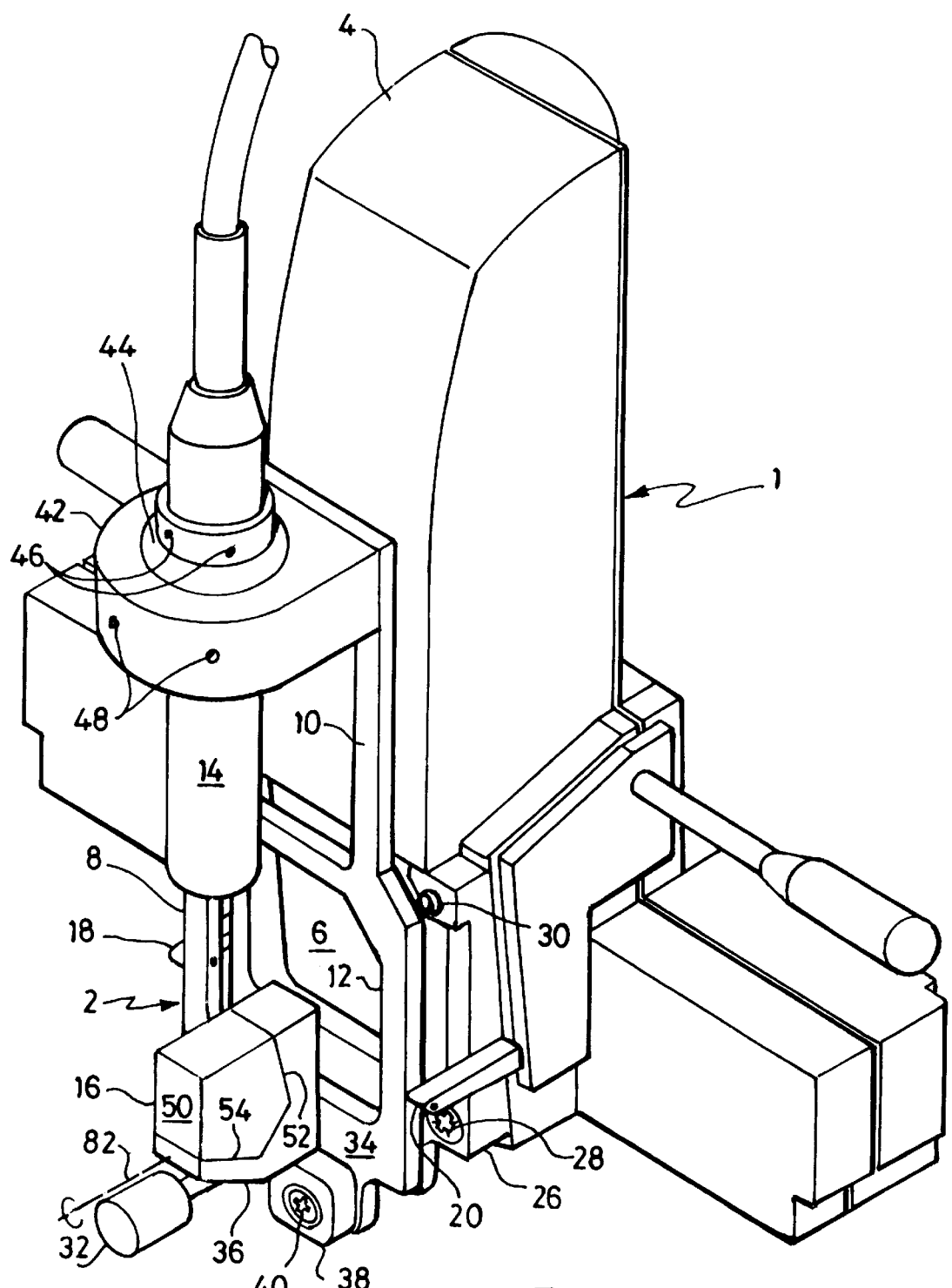
FIG. 1 is a perspective view of an ophthalmoscope and attachment according to the invention.

With reference to FIG. 1, reference numeral 1 generally denotes an indirect ophthalmoscope which, in this example, is of the type currently supplied by the Applicants under the Trade mark KEELER VANTAGE. This ophthalmoscope can be retrofitted with an attachment, generally referenced 2, to provide an ophthalmoscope in accordance with the invention.

The ophthalmoscope 1 is provided with a headset (not shown) to enable the ophthalmoscope to be mounted on the head of a user, and has a housing 4 for a light source, and illuminating optics.

Figure 2:
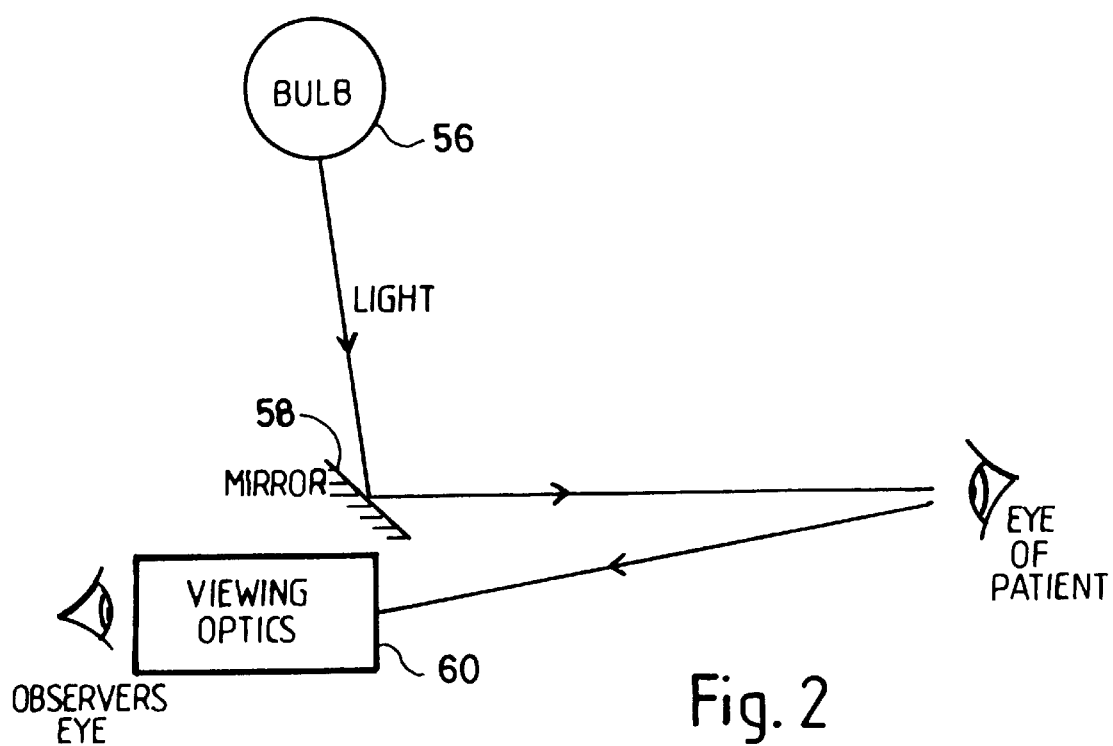
FIG. 2 is a schematic side view of the illuminating optics of the ophthalmoscope.

With reference to FIG. 2, the illuminating optics comprise a light bulb 56, light from which is reflected from an angled planar mirror 58 in the housing 10, to an eye to be examined (indicated as the "eye of patient"). Light from the patient's eye travels back to the ophthalmoscope to enter the viewing optics of the latter. Reference numeral 60 denotes the viewing optics, some components of which are shown in more detail in FIG. 4, and are described below.

The front of the housing 4 includes a window 6 through which light from the illuminating optics exits the housing 4, and light from the eye under examination reaches two spaced apart light receiving elements of the binocular viewing optics.

In use, the illuminating light beam is reflected from the planar mirror 58 and passes through a hand-held lens (usually plus 20D) before reaching the patient's eye. The user of the ophthalmoscope views the illuminated eye through the binocular viewing optics. The illuminating beam path does not coincide with the path of light reflected from the eye into the viewing optics since there is vertical separation and an acute angle between those two paths.

The viewing optics 60 include two light receiving elements, each comprising a respective one of two mirrors 62 and 64 mounted on triangular mirror blocks 66 and 68 which are, in turn, supported on a platform 70. The platform 70 also supports two further, triangular mirror blocks 72 and 74 positioned one on either side of the mirrors 62 and 64. The further blocks carry corresponding further mirrors 76, 78 (also part of the viewing optics) and have apertures (eg 80) to allow light reflected from the mirrors 62 and 64 to travel to the reflective surfaces of mirrors 76 and 78 from which the light is reflected into eye pieces (not shown) forming part of the viewing optics and situated behind the platform 70.

All the mirror blocks 66, 68, 72 and 74 are all slideably mounted on the platform 70, and the ophthalmoscope includes mechanisms, not shown, for varying the separation between the blocks 66 and 68 (to adjust the stereopsis of the ophthalmoscope) and between the blocks 72 and 74 to enable the ophthalmoscope to accommodate a range of different interpupillary distances of its users.

The attachment 2 comprises a frame 8 having upper and lower generally rectangular portions, respectively referenced 10 and 12. The upper portion carries a camera 14, whilst a penta prism 16 is mounted at the bottom of the lower portion 12.

The frame 8 is pivotally connected to a pair of opposed arms 18 and 20 which are in turn attached to a rectangular mounting frame 26 adapted to be attached to the front of the ophthalmoscope 1. The top of the mounting frame 26 has two spaced apart tongues (not visible in FIG. 1) which slide up under the front vents of the ophthalmoscope 1. The bottom portion of the frame 26 has two apertures, one on either side, for receiving respective screws, one of which is shown at 28. The screws extend into screw-threaded bores in the front of the ophthalmoscope 1 so that the frame 26 is securely located on the latter.

As can be seen prom FIG. 1, both the frame 26 and the portion 12 have central openings in registry with the window 6.

Two compression springs, one of which is shown at 30, are situated towards the top of the portion 12 and the mounting frame 26, and act between the frame 8 and the mounting frame 26 to bias the top of the frame 8 away from the ophthalmoscope 1, and hence the portion of the frame 8 below the pivotable arms 18 and 20, towards the mounting frame 26. The extent of movement towards the mounting frame 26 is limited by an adjustment screw 32 which extends through a screw-threaded through bore in a cross-member 34 at the bottom of the portion 12 to bear against the mounting frame 26. The screw 32 is thus urged against the mounting frame 26 by the springs 30, and the rotation of the screw 32 will cause the frame 8 to pivot around the pivotal connections at the arms 18 and 20, and hence about a horizontal axis passing through those connections.

The prism 16 is securely held within a bracket 36 from which an apertured lug 38 extends. The lug 38 is, in turn, screwed onto the bottom of the portion 12 using a screw 40. The screw shaft is of a smaller aperture than the aperture, and a pin (not shown) extends from the bracket 36 into the bottom portion 12. This mode of attachment of the prism 16 enables the position of the latter to be adjusted by loosening the screw 40 and rotating the bracket 36 about the axis of the pin before tightening the latter to fix the orientation of the prism 16. The axis about which the bracket can rotate is indicated at 82 in FIG. 1.

Figure 3:
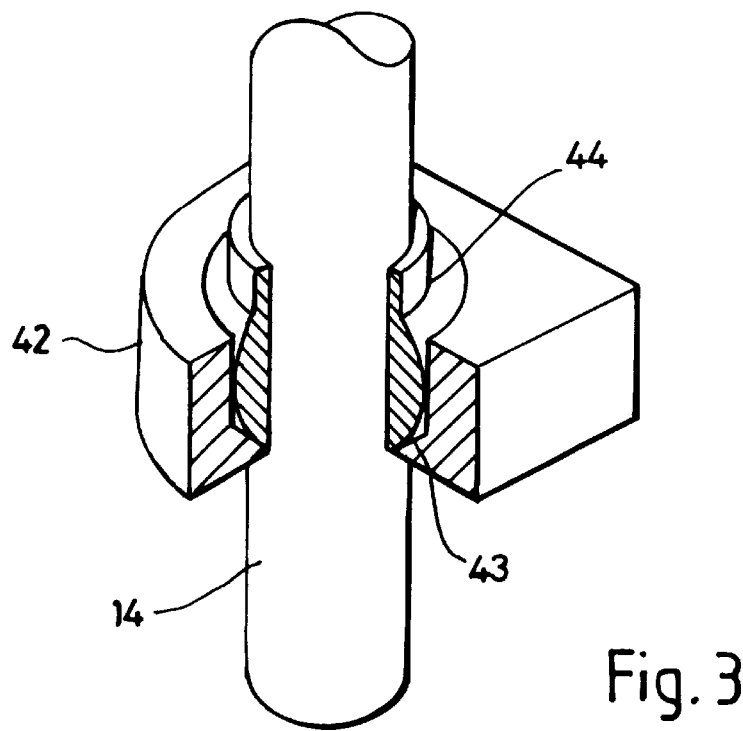
FIG. 3 is a more detailed, cut-away view of part of the ophthalmoscope.

With reference to FIGS. 1 and 3, a further bracket 42 extends forwardly from the top of the portion 10 and includes a vertical passage 43 having a cylindrical upper portion and a frustoconical lower portion. The passage 43 accommodates a ball sleeve 44 through which the camera 14 extends and is securely fixed thereto by-means of two grub screws 46. The ball sleeve 44 can move within the passage in the bracket 42 to allow the orientation of the camera 14 to be adjusted. Once a suitable orientation has been selected, the position of the ball sleeve 44 relative to the bracket 42 is fixed by means of a pair of radial grub screws 48 which have pointed ends for engaging the exterior of the ball sleeve 44 to hold the latter in position.

A compression spring and ball (not shown) act between the ball sleeve 44 and the passage 43 to hold the sleeve captive in the passage even when the screws 48 are removed.

As can be seen from FIG. 1, the prism 16 is centrally located on the bottom portion 12 of the frame 8. When the separation between the mirrors 62 and 64 is at a minimum, the prism holder 36 does partially occlude the two mirrors 62 and 64. However, when the stereopsis is set at a maximum, so that the separation between the mirrors 62 and 64 is also at a maximum, the mirrors 62 and 64 are laterally spaced, in their entireties, in opposite directions from the prism 16 and the holder 36. Consequently, when the ophthalmoscope 1 is viewed from the front, the prism 16 would appear between the two mirrors. As a result, the user of the ophthalmoscope looks past either side of the prism 16.

Figure 4:
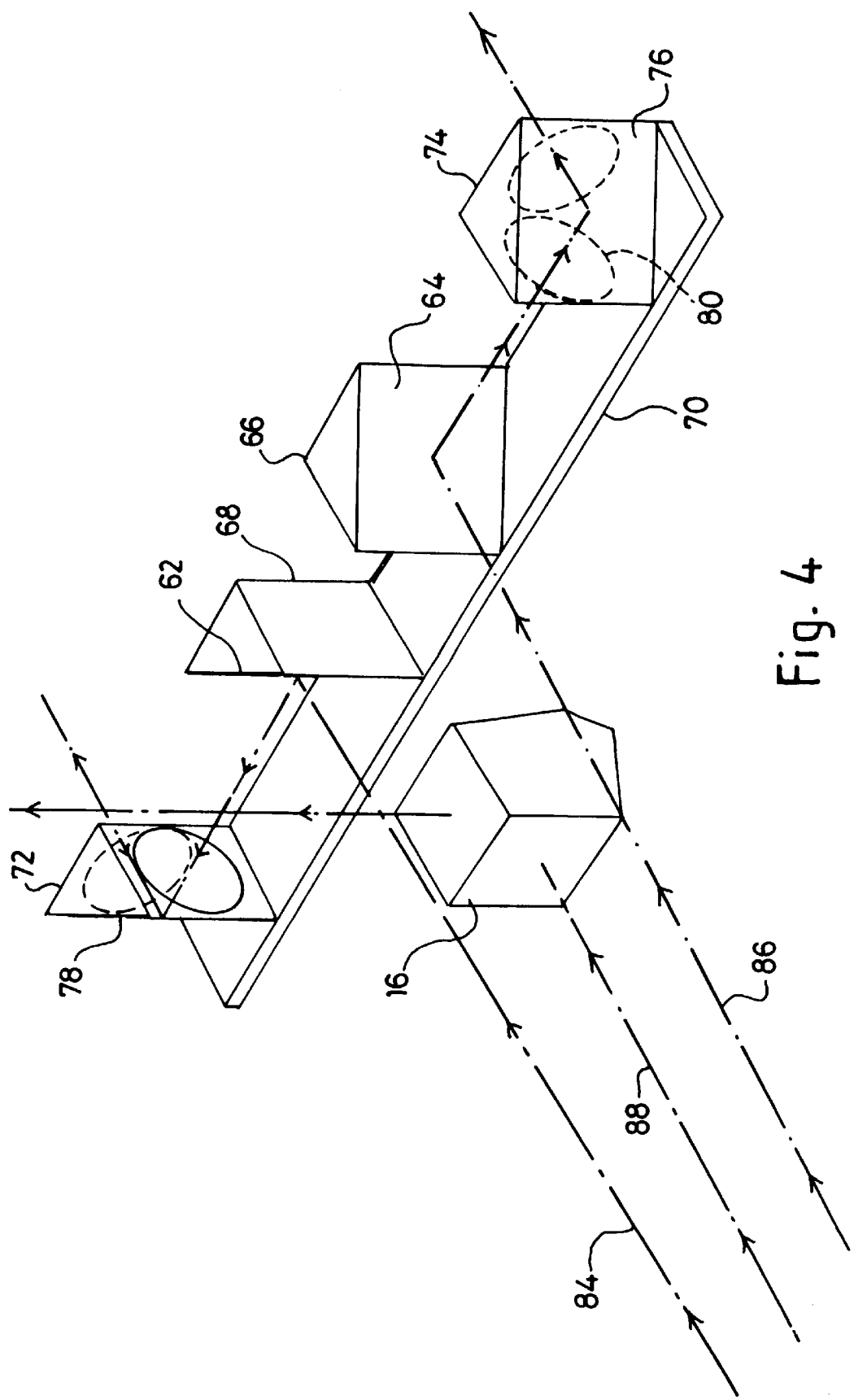
FIG. 4 is a simplified diagram illustrating the relative positions of parts of the viewing optics and image capture means of the ophthalmoscope.

This can be seen from FIG. 4, in which the separation between the mirrors 62 and 64 is such that light travelling from the eye under examination to the viewing optics travels along paths, for example paths 84 and 86 which straddle the prism 16, whilst the camera 14 receives light, reflected by the prism 16, which has travelled along paths, for example path 88, which are laterally spaced from the mirrors 62 and 64, and hence from the path of light thereto.

Light from an eye under examination enters the prism 16 through a front face 50 and travels to a rear upper-angled face 52 which reflects the light down and forward onto a further angled face 54. The face 54, in turn, reflects light from the face 52 directly up into the camera 14. Consequently, the image of the eye under examination is reflected firstly by the face 52 and then by the face 54 before entering the camera 14. As a result of this double reflection, the image entering the camera 14 is not inverted relative to the view seen through the viewing optics of the ophthalmoscope 1.

In this example, the prism is sold under the Trade Mark MELLES GRIOT and is identified by the reference 01PPA003. The video camera is identified by the Trade Mark "TELI" and produced by Tokyo Electronic Industry Co. Limited. The present example has a product number CS6100, and uses a PML 300-30 mms focal length lens.

It has been found, in practice, that not all users of the ophthalmoscope look straight into the eyepieces of the viewing optics For example, a wearer of half -moon spectacles, may tilt his/her head forwards relative to the ophthalmoscope so as to view the eye under examination (through the viewing optics) over the tops of the spectacles, Consequently, the image detected by the camera 14 may not correspond with that being viewed by the user. However, this difference can be eliminated by using the screw 32 to pivot the frame 8 about the pivotal connection to the arms 18 and 20 until the rays of light which the prism 16 reflects up into the camera 14 are substantially co-planar with those received by the viewing optics. Before the ophthalmoscope is first used with the attachment 2, the attachment 2 is set up by locking the prism 16 and camera 14 in a suitable relative position. This can be achieved with, for example, a suitable jig.

The ophthalmoscope described above is one example of an embodiment of the invention, and various alterations or modifications may be made without departing from the scope of the invention as defined by the claims. Thus, for example, the prism 16 may be replaced by an alternative type of reflecting means, for example a mirror. In such a case, the camera will receive a laterally inverted image, which may be displayed on a monitor or may be electronically re-inverted by image processing circuitry connected between the camera and the monitor.

Furthermore, instead of the frames 8 and 26, the ophthalmoscope may have an alternative type of mount, for example formations which attach the camera and reflector directly to the ophthalmoscope, which enable the position of the camera and reflector to be altered and which therefore also constitute the adjustment means.

What is claimed is:

1. An ophthalmoscope having viewing optics through which, in use, an eye under examination is viewed, the optics having at least one light receiving element via which light from an eye under examination is received by the viewing optics, the ophthalmoscope further compromising image detecting apparatus for detecting an image of an eye under examination, wherein the image detecting apparatus is substantially centrally positioned on the ophthalmoscope and is so positioned relative to the light receiving element that, in use, light from the eye under examination which is incident on the image detecting apparatus is received by the latter at a position which lies in substantially the same horizontal plane as the light receiving element of the viewing optics, wherein said position at which the image detecting apparatus receives light is laterally spaced from the paths of light from the eye to the light receiving element or through the viewing optics.

2. An ophthalmoscope according to claim 1, in which the image detecting apparatus comprises a reflector, on which light to form the image is incident, and a camera into which said incident light is reflected by the reflector.

3. An ophthalmoscope according to claim 2, in which the ophthalmoscope is a binocular instrument, having two spaced apart light receiving elements each for directing light into a respective eye of the user, the reflector being so situated that the elements are at least partially spaced in opposite lateral directions therefrom and in which the elements and the reflector are substantially co-planar.

4. An ophthalmoscope according to claim 3, in which the separation of the elements of the viewing optics is adjustable to adjust the stereopsis of the ophthalmoscope, substantially all of each element being laterally spaced from the portion at least when the separation of the objectives is at its maximum.

5. An ophthalmoscope according to claim 4, in which the reflector is equidistant from the elements.

6. An ophthalmoscope according to claim 5, in which the camera is equidistant from the light receiving elements.

7. An ophthalmoscope according to claim 6, in which the camera is positioned above the light receiving elements, and the reflector reflects light up into the camera.

8. An ophthalmoscope according to claim 7, in which the reflector is so arranged as to cause two reflections of light from the eye under examination so as to eliminate any mirror inversion of the image detected by the camera.

9. An ophthalmoscope according to claim 8, in which the reflector comprises a pentagonal prism.

10. An ophthalmoscope according to claim 9, in which the prism and camera are carried by a frame adapted to be mounted on the front of the ophthalmoscope.

11. An attachment for an ophthalmoscope, the viewing optics of which have at least one light receiving element via which light from an eye under examination enters the viewing optics, the attachment comprising retaining member for holding a camera and a reflector operable to reflect light from any eye under examination into a camera held by the retaining means, the attachment further comprising a mount for mounting the attachment on an ophthalmoscope, wherein the position of the reflector relative to the mount is such that, when mounted on an ophthalmoscope, the reflector is, in use, at substantially the same level as said element, wherein the attachment is adapted for use with a binocular ophthalmoscope, and the retaining member comprises a frame having a cross-member on which the reflecting means is mounted in a generally central position such that, with the attachment mounted on the ophthalmoscope, the two light receiving elements of the latter are laterally spaced, in opposite directions, from the reflecting means.

12. An attachment according to claim 11, in which the reflecting means comprises a pentagonal prism, for example a penta prism.

* * * * *